United States Patent [19]

Boulaud et al.

[11] Patent Number: 5,939,649

[45] Date of Patent: Aug. 17, 1999

[54] DYNAMIC MOBILITY SELECTOR FOR AEROSOL PARTICLES

[75] Inventors: Denis Boulaud, Paris; Michel Pourprix, Nontlhery, both of France

[73] Assignee: Commissariat a l'Energie Atomique, Paris, France

[21] Appl. No.: 08/795,796

[22] Filed: Feb. 5, 1997

[30] Foreign Application Priority Data

Feb. 15, 1996 [FR] France .................................. 96 01869

[51] Int. Cl.$^6$ .................................................. G01N 15/02
[52] U.S. Cl. .................. 73/865.5; 55/447; 95/34
[58] Field of Search ................ 73/865.5; 95/34; 55/447

[56] References Cited

U.S. PATENT DOCUMENTS

| | | | |
|---|---|---|---|
| 4,657,667 | 4/1987 | Etkin | 209/135 |
| 5,117,190 | 5/1992 | Pourprix | 324/457 X |
| 5,150,036 | 9/1992 | Pourprix | 324/601 X |
| 5,592,096 | 1/1997 | Pourprix | 324/452 |
| 5,596,136 | 1/1997 | Flagan et al. | 73/28.04 |
| 5,621,208 | 4/1997 | Pourprix | 250/287 |

FOREIGN PATENT DOCUMENTS

| | | |
|---|---|---|
| 0 159 002 | 10/1985 | European Pat. Off. . |
| 0 685 725 | 12/1995 | European Pat. Off. . |
| 0 685 727 | 12/1995 | European Pat. Off. . |

OTHER PUBLICATIONS

Journal of Aerosol Science, vol. 15, No. 4, pp. 491–502, 1984, W.D. Griffiths, et al., "An Aerodynamic Particle Size Analyzer Tested with Spheres, Compact Particles and Fibres Having a Common Settling Rate Under Gravity" Month Not Given.

Journal of Aerosol Science, vol. 11, pp. 139–150, 1980, James Wilson, et al., "Aerodynamic Particle Size Measurement by Laser–Doppler Velocimetry" Month Not Given.

Proceedings of the Annual Conference of the GaeF, pp. 222–223, J.K. Agarwal, et al., "Real–Time Aerodynamic Particle Size Analyzer" 1982 Month Not Given.

*Primary Examiner*—Thomas P. Noland
*Attorney, Agent, or Firm*—Oblon, Spivak, McClelland, Maier & Neustadt, P.C.

[57] ABSTRACT

The invention concerns a dynamic particle mobility selector comprising two separate and parallel coaxial disks (30, 32) defining a dynamic selection zone (31), the upper disk comprising an annular slit with radius $r_1$ and a central suction intake (38) in order to circulate a laminar, centripetal and stable air flow in the dynamic selection zone. An annular opening (36) with average radius $r_2<r_1$ may be provided in the lower disk (32). Application to a dynamic mobility spectrometer, to a device for measuring the particle size of an aerosol and a mono-dispersed aerosol generator.

10 Claims, 3 Drawing Sheets

DYNAMIC MOBILITY SELECTOR FOR AEROSOL PARTICLES

DESCRIPTION

Technical Field and Prior Art

The invention relates to the field of selecting and/or characterization of aerosols, particularly for super-micronic particles (particularly in the 2 to 20 μm range).

There are many devices available for on-line measurement of the particle size distribution in the field of micronic and sub-micronic aerosol metrology. For example, there are devices that use electrical methods, and particularly differential electrical mobility analyzers, optical methods, and aerodynamic methods that provide a size distribution based on the electrical mobility of particles, the optical properties of particles and particle inertias, respectively.

Aerodynamic methods must be used if it is required to characterize the inertial behavior of an aerosol for super-micronic particles. The devices most frequently used implement an impactor, or a cyclone, or a centrifuge, or a sedimentation chamber. In general, these devices only have a mediocre size resolution capacity, and it is necessary to take a sample and then carry out a subsequent analysis in order to determine the particle size. Therefore, measurement processes are long, expensive and tedious, and cannot provide the required information on-line.

Therefore, there is a need for devices capable of characterizing the aerodynamic behavior of particles, and providing on-line particle size of an aerosol with a very good sizing resolution.

Before describing known embodiments of this type of equipment in more detail, it is worth recalling that the dynamic mobility, B, of a particle of diameter $d_p$ is written:

$$B = \frac{1}{3\pi\mu d_p} \quad (1)$$

where $\mu$ is the dynamic viscosity of the carrier gas.

When the particle diameter is close to the average free path of molecules in the fluid, 1, the medium can no longer be considered as being continuous and a correction term $C(d_p)$ is introduced. The dynamic mobility is then written:

$$B = \frac{Cd_p}{3\mu\pi d_p} \quad (2)$$

where $$Cdp = 1 + Kn\left[1.257 + 0.4\exp\left(\frac{-1.1}{Kn}\right)\right] \quad (3)$$

and $$Kn = \frac{2l}{d_p} \text{ is the Knudsen number.} \quad (3')$$

The product of the particle mass m and the dynamic mobility gives the relaxation time τ.

$$\tau = mB = \frac{d_p^2 \rho_p^2 C(d_p)}{18\mu} \quad (4)$$

where $\rho_p$, is the particle density.

ρ characterizes the time required for a particle to adjust its speed to a new force field or to a new acceleration caused by variations of the fluid speed vector.

If Stokes law is applicable, the fall or the sedimentation speed is written simply:

$$V_s = mBg = \rho g \quad (5)$$

Starting from the particle sedimentation speed, the concept of the equivalent aerodynamic diameter was created; this is the diameter of a sphere with density 1 and the same sedimentation rate as the particle considered (the diameter $d_a$ for which π=1 in formula (4) above).

At the present time there are two types of known devices capable of providing the particle size characteristic of the aerodynamic behavior on line and with good resolution.

The first of these devices was described in articles by J. C. WILSON et al published in the "Journal of Aerosol Science", vol. 11, pp 139–150, 1980, and by J. K AGARWAL et al, published in "Proceedings of the Annual Conference of the GAeF", pp 222–223, 1982. FIG. 1 shows a diagram of this device. In this figure, references 2 and 4 refer to an inner tube and an outer tube respectively, each terminated by an inner orifice 6 and an outer orifice 8. The aerosol carrying the particles to be characterized is strongly accelerated by passing through orifice 8. Due to their inertia, characterized by their relaxation time ρ, the particles will take some time before adjusting their speed to the speed of the carrier fluid, this adjustment delay being proportional to the aerodynamic diameter. Thus the aerodynamic diameter may be determined by measuring the speed of each particle immediately after orifice 8. The speed is measured using the split laser beam 10, which forms two points through which the particles pass. Each particle thus produces two light pulses converted into electrical pulses by photo-multiplier 12. The time between the two pulses is measured by a clock with a resolution capacity of 2 ns. For an 0.5 μm diameter particle, the flight time is 800 ns, and it may be as high as 5000 ns for a large 30 μm particle, this range already being covered by this device also called "APS" (Aerodynamic Particles Sizer).

An advantage of this device is its very good resolution capacity and its automatic operation.

One problem related to this device is that solid and liquid particles with the same aerodynamic diameters do not give the same response; since liquid particles are deformed under the effect of the sudden acceleration in the orifice. Difficulties may also occur in measuring the fibers. Furthermore, this device determines a relaxation time when a sudden acceleration occurs in the flow. Under these conditions, the elapsed relaxation time at the aerodynamic diameter is not always obvious, and will depend on the stiffness and shape of the particles. Finally, this device cannot be used as a mono-dispersed aerosol generator, particularly for super-micronic particles.

Another device is described in an article by W. D. GRIFFITHS et al., published in the "Journal of Aerosol Science", vol. 15, No. 4, pp. 491–502, 1984. This device is of the "TIMBRELL" type. It can precisely classify particles as a function of their aerodynamic diameter. The principle of this equipment will be described with reference to FIG. 2. The particles of an aerosol are inlet through a small tube 20 into a laminar flow 22 of clean air which will lead the particles towards a sedimentation chamber 24. This chamber is in the form of a wedge with a constant height. The particles may form a sediment on the lower part 26 of the chamber, which is horizontal, as a function of their aerodynamic diameter. In a first version of the "TIMBRELL" device, particles are recovered on optical microscope slides for subsequent analysis.

The device was modified, particularly as described in the article by W. D. GRIFFITHS mentioned above, in order to be able to extract particles with a well defined diameter, and to detect them on line. In particular, the modification proposed in this document is sufficient to select four particle dimensions between 1 and 8 μm. This modified device is still very difficult to use, and so far it has been impossible to make any commercial development. One of the problems that arises with the "TIMBRELL" type device is that it cannot give a good laminar flow of the air in which the particles are input. Furthermore, this device is quite bulky.

DESCRIPTION OF THE INVENTION

The invention proposes a new dynamic mobility selector for particles in an aerosol contained in an atmosphere, in particular capable of solving the problems above.

More precisely, the purpose of the invention is a dynamic mobility selector for aerosol particles contained in an atmosphere, characterized in that it comprises:

two separate and parallel coaxial disks, the space between the two disks defining a dynamic selection zone communicating with the atmosphere to be examined through an annular slit of radius $r_1$ formed in the first disk, a central intake in which a laminar, centripetal and stable air flow circulates in the dynamic selection zone.

An annular opening with average radius $r_2$ ($r_2 < r_1$) may be provided in the second disk.

In this device, particles are introduced through a slit radius $r_1$ located above the selection zone, and are lead towards the second disk located in the lower part of the selection zone (through the extraction slit if there is an extraction slit). Particle movement takes place only under the combined action of an air flow between the two disks and the gravity field.

Due to the structure with circular symmetry, the device according to the invention enables a perfectly laminar, stable and controlled radial flow. Furthermore, it is very compact.

It can provide a direct value of the relaxation time, the dynamic mobility and the particle sedimentation speed, which is simply related to the relaxation time (relation Vs=ρg) and which defines the equivalent aerodynamic diameter. On the other hand, an APS type of instrument determines a relaxation time when a sudden acceleration occurs in a flow, and it is not easy to determine the aerodynamic diameter from the relaxation time.

The result is that the device according to the invention can select particles of the same aerodynamic diameter. Therefore the selector can advantageously be used as a mono-dispersed aerosol generator, particularly for super-micronic aerosols. This aerosol generator function is impossible with an APS type instrument.

Another particular problem solved by this invention is related to the fact that after extraction through the selection slit, particles no longer necessarily have the same trajectories.

Consequently, there is a spread in the transit time and some dispersion through the instrument and its particle extraction means, which can be harmful in some applications.

In one specific embodiment, this problem is solved if the selector also comprises:

a third disk located facing the second disk, means of injecting a radial and laminar air flow into the space between the second and third disks, from the periphery of the second and third disks, a central extraction orifice formed in the third disk.

Therefore in this configuration, a second stage is made using third and second disks, and what is called a "dynamic confinement" is made by means of a filtered air flow between these two disks. This flow directs particles immediately that they are extracted from the first stage. The particles then exit from the second stage, and are transported in a duct transferring them towards the outside, still in laminar flow, with the special feature that they are confined to remain close to the center of the flow, without any contact with the walls (and therefore without any losses) and with identical trajectories (and therefore with identical transit times).

According to another specific embodiment, the extraction slit may consist solely of a central orifice.

The selector with a central extraction orifice is simpler to make than devices with an annular extraction slit, and gives better performances and a shorter transit time in the particle extraction circuit. It avoids sedimentation problems in this circuit.

Means may also be provided to maintain the space between the first two disks under low pressure. This means that the relaxation time, and therefore the sedimentation speed, can be increased for fixed particle sizes.

Means may also be provided for varying the laminar, centripetal and stable air flow $Q_0$. Thus, different aerodynamic diameters can be selected.

The invention also concerns a dynamic mobility spectrometer for particles of an aerosol contained in an atmosphere, comprising a dynamic mobility selector equipped with flow $Q_0$ variation means as described above, and means of detecting the selected particles.

It is advantageous if these detection means are optical.

The invention also concerns a device for measuring the particle size of aerosols as a function of their aerodynamic diameter, comprising a dynamic mobility selector as described above, means of varying the laminar, centripetal and stable air flow, means of detecting the selected particles, and means of calculating the aerosol particle size.

Another purpose of the invention concerns a process for selecting the dynamic mobility of particles of an aerosol contained in an atmosphere, characterized in that it comprises:

introduction of the aerosol into a dynamic selection zone consisting of the space located between two separate and parallel disks, and through an annular slit of radius $r_1$ formed in the first disk, suction of an air flow $Q_0$ through a central intake, in order to circulate a laminar, centripetal and stable air flow in the dynamic selection zone, the particle movement taking place solely under the action of this air flow and the gravity field.

Particles may be selected through an annular opening with average radius $r_2$ ($r_2 < r_1$), formed in the second disk.

The advantages of this process are the same as described above for the dynamic mobility selector according to the invention.

A third disk may be located facing the second disk, and may be equipped with a central extraction orifice, a radial and laminar air flow circulating in the space between the second and the third disk starting from their periphery. This process then provides a laminar particle flow, while confining them close to the center of the flow, without any contact with the walls and with identical trajectories.

In particular, the opening formed in the second disk may consist solely of a single central extraction orifice. In this case, the process is easier to make, gives better performances with fewer particle losses (particularly by sedimentation) and a shorter transit time in the extraction circuit.

The selection zone may operate at low pressure in order to increase the dynamics of the device for sub-micronic particles.

The invention also relates to a process for making a dynamic mobility spectrum for particles in an aerosol contained in an atmosphere, making use of a dynamic particle mobility selection process such as that described above, means of varying the flow $Q_0$, and detection of selected particles, for example using optical means.

A process according to the invention for measuring the aerosol particle size as a function of their aerodynamic diameter comprises a selection process as described above, detection of the selected particles, and a step to calculate the aerosol particle size.

BRIEF DESCRIPTION OF THE FIGURES

In any case, the characteristics and advantages of the invention will be more obvious after reading the following description. This description concerns example embodiments given for explanatory purposes but which are in no way restrictive, referring to the drawings in the appendix in which.

DETAILED DESCRIPTION OF EMBODIMENTS OF THE INVENTION

Figure 1:
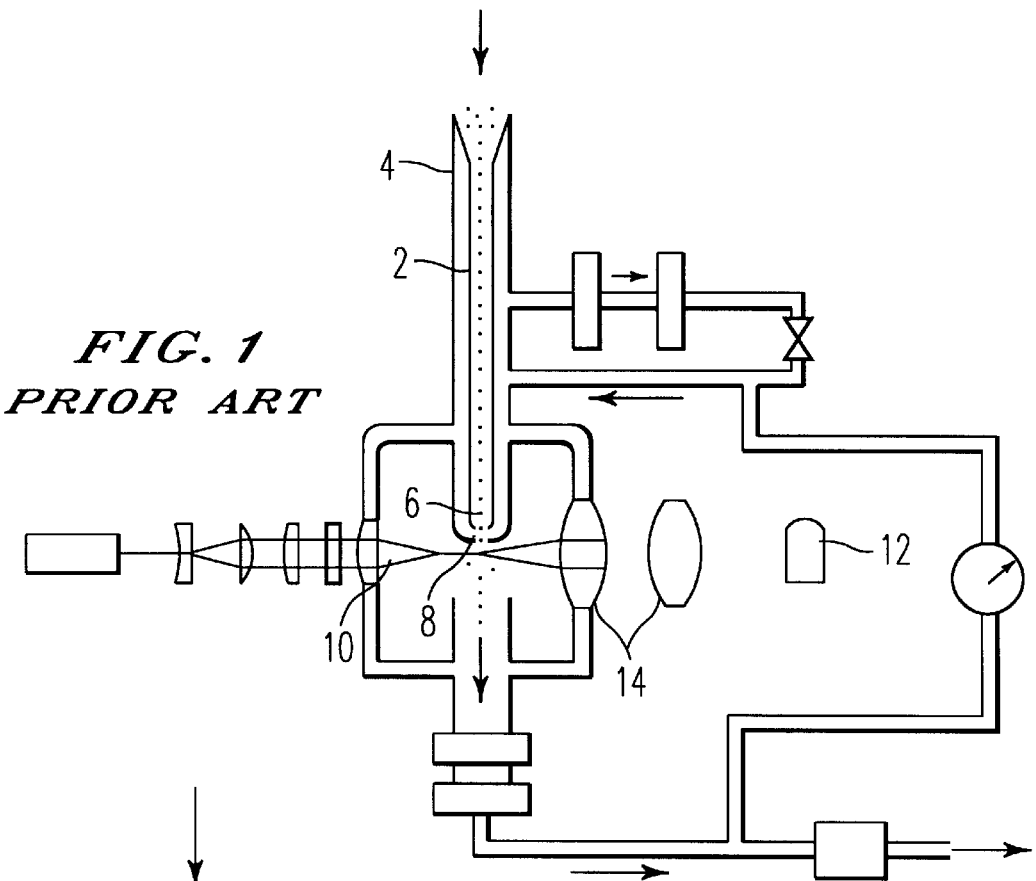
FIGS. 1 and 2, already described, show devices according to prior art used for on line determination of the particle size characteristic of the aerodynamic behavior of an aerosol.
Figure 2:
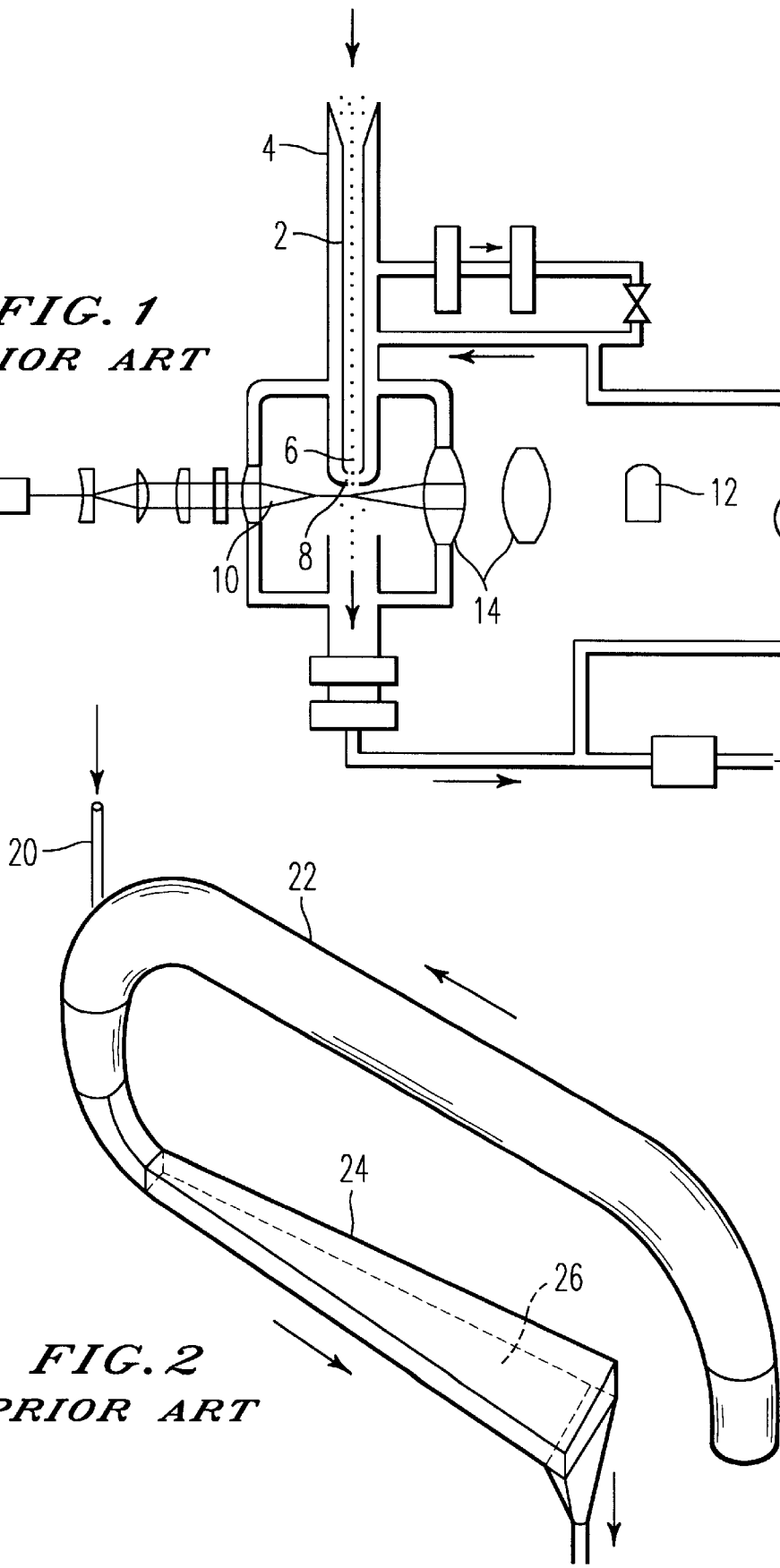
Figure 3A:
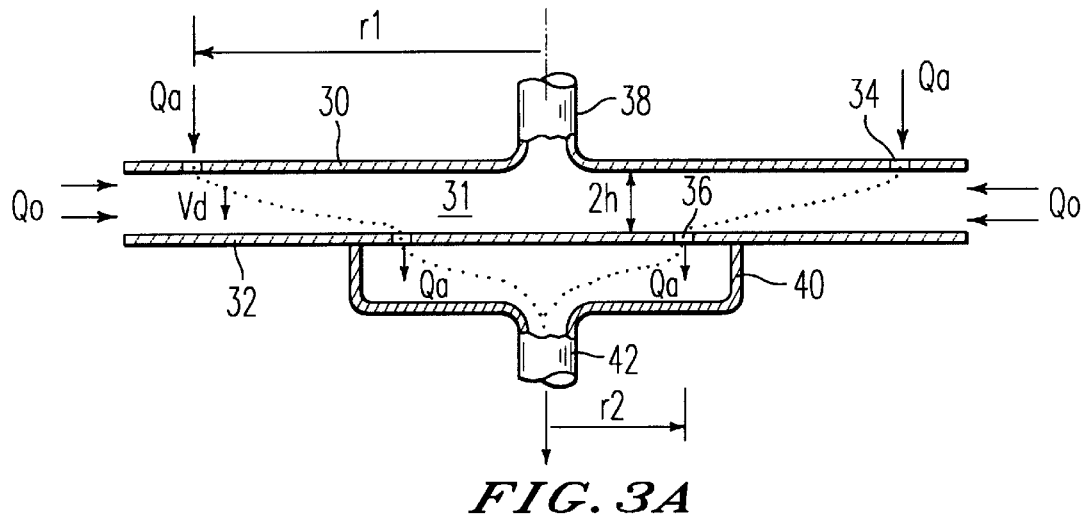
FIGS. 3A and 3B show two variants of a dynamic mobility selector according to the invention.

A first embodiment of a dynamic aerosol particle mobility selector according to the invention will now be described in relation to FIG. 3A. In this figure, references 30 and 32 refer to two horizontal, parallel and concentric disks defining a "dynamic selection zone" 31 between them. The upper disk 30 has an annular slit 34 with radius $r_1$ through which an aerosol is introduced with a flow $Q_a$. A central intake tubing 38 formed in the upper disk 30 extracts an air flow $Q_0$ from the dynamic selection zone 31. An annular opening 36 with a radius $r_2$ ($r_2 < r_1$) is formed in the second disk 32. When the instrument is in operation, a flow $Q_a$ of selected particles passes through this slit 36. An entrainment gas (usually filtered air) is injected between the two disks around he periphery of the space 31, by means not shown in FIG. 3A. Due to the circular structure of the equipment, a laminar flow $Q_0$ circulates between the two ducts up to the intake tube 38.

Selected particles can then be directed through a box 40, such as a cylindrical box, and a pipe 42, towards any type of device suitable for the envisaged application, for example a particle counter to be calibrated with graded and produced particles, or to a detector such as an optical detector.

It is also possible to collect selected particles in a collector, for example a mechanical collector. This type of mechanical collector comprises a box such as box 40 and a porous membrane in which the particles are deposited. The membrane may then be analyzed, for example by weighing.

In one variant, the central intake duct 38 is formed in the lower disk 32 and passes through the box 40.

Particles move from the inlet slit 34 to the outlet slit 36 under the combined action of:
a filtered, radial and laminar air flow $Q_0$ set up between the two disks, the gravity field, which induces a drift speed $V_d$; this drift speed is equal to the particle sedimentation speed in the special case in which the disks are kept horizontal.

It can be demonstrated that particles selected through slit 36 at flow $Q_a$ have a relaxation time $\rho$ given by the equation:

$$\tau = \frac{Q_o}{\pi g(r_1^2 - r_2^2)} \pi \tag{6}$$

where g is the acceleration due to gravity.

The drop or sedimentation speed is then written simply as $V_s = \rho g$.

The equivalent aerodynamic diameter can be obtained from the particle sedimentation speed using formulas (6) and (4) above ($\rho = 1$ in equation (4)).

Consequently, the device can be used to select particles with a given dynamic mobility, a given relaxation time and therefore a given sedimentation speed and a given aerodynamic diameter, provided that the flow $Q_0$ and the geometric characteristics of the equipment are known. Since the geometric characteristics are fixed, it is only necessary to vary the flow $Q_0$ to select the particles with different relaxation times, and therefore different sedimentation speeds, and therefore different aerodynamic diameters. Therefore the device is perfectly suitable for making a mono-dispersed aerosol generator: when it is required to produce particles with a given diameter, all that is necessary is to calculate the flow $Q_0$ to be imposed on a device with given geometric characteristics.

Particle extraction through an annular slit 36 requires the use of a box 40 between the slit and the extraction duct 42. Particle transport through circuits in the system may be the cause of losses by diffusion in the vicinity of the walls, and losses by sedimentation, particularly in box 40. Furthermore, the transit time in this box, which may be long, is not the same for all particles and consequently a certain amount of dispersion takes place through the device, which may be a disadvantage in some applications.

Figure 3B:
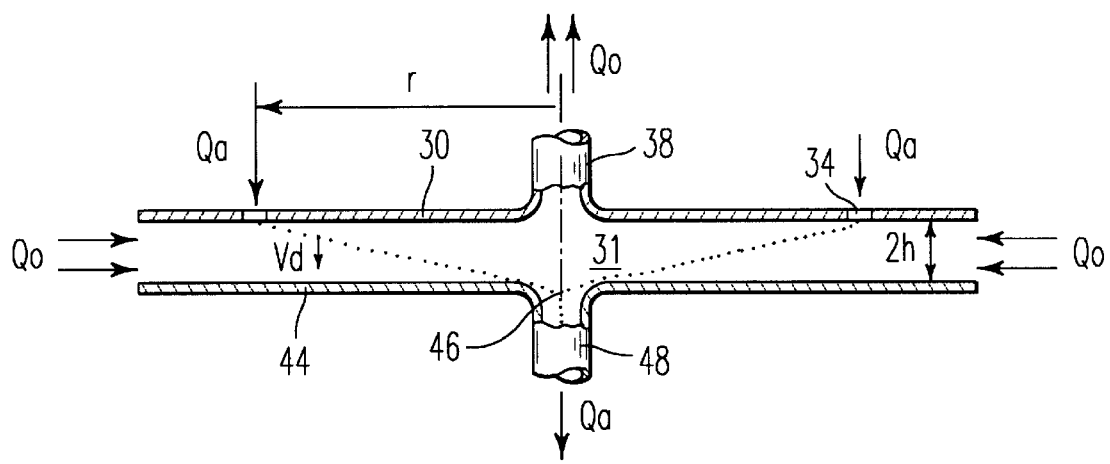

A second embodiment which will be described in relation to FIG. 3B, solves this problem. This second device operates based on the same principles as the first device, essentially with the same elements, but the annular extraction slit in the lower disk 44 is reduced to a single central circular orifice 46. This orifice opens up into an extraction duct 48. Identical references in FIGS. 3B and 3A refer to the same elements.

In this case too, the extraction orifice 46 may outlet onto a collector, for example a mechanical collector.

The central extraction orifice 46 is a singular point in the flow since it is the point at which laminar flow ceases. Particles which deposit on the center of the second disk 44 are drawn in through this orifice 46 with a flow $Q_a$. These particles have a relaxation time $$\tau = \frac{Q_o}{\pi g r_1^2}.$$

The diameter $\phi$ of this orifice 46 is preferably chosen to give good particle selectivity (the selectivity is low if the diameter is large), and also to not disturb the fluid flow passing through it (a "jet" phenomenon occurs at this orifice if the diameter is small). This central extraction device guarantees less particle losses after their exit from the selector, and a shorter transit time in extraction circuits.

The device according to the invention was presented with a disk 32, 44 equipped with a selection opening (slit or orifice). This disk can also be replaced by a solid disk. In this case, the particles are deposited on this solid disk, and particles deposited at an arbitrary distance r from the center line of the device have a relaxation time given by equation (6), where $r_2$ is replaced by r.

Figure 4:
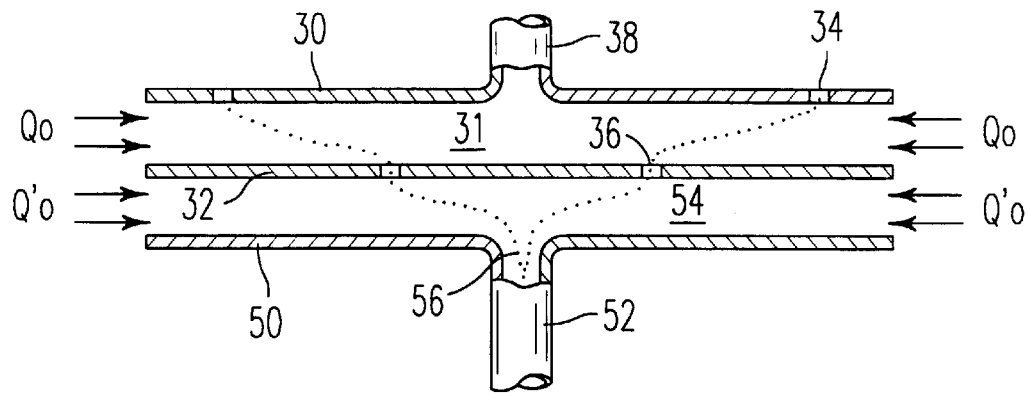
FIG. 4 shows a variant of a device according to the invention.

Another variant that may be used with either of the two embodiments illustrated above is illustrated in FIG. 4. The upper part (or first stage) of the device is identical to the upper part of the device shown in FIG. 3A.

A second stage collects particles with the same dynamic mobility selected by the first stage. This second stage is composed firstly of a second disk 32 already described above, and secondly a third disk 50 facing the second disk and defining a space 54 with the second disk. Starting from the periphery of this space 54, it is possible to impose a filtered and radial air flow $Q'_0$, using means known to those skilled in the art. $Q'_o$ is chosen such that the air flow in the second stage is laminar. Thus particles selected through opening 36 are directed after they are extracted from the first stage.

The third disk 50 has an opening 56 at its center that leads onto a duct 52. The center of the opening 56 is preferably aligned with the centers of disks 32 and 30. Selected particles continue their laminar flow, and are confined to the vicinity of the center of flow along the center line of the opening 52, without coming into contact with the walls. Furthermore, the trajectories followed by the particles are identical in all parts of the equipment, even in the second stage and in duct 52, therefore the particles flow with identical transit times which are easy to determine since the geometric dimensions of the system are easy to determine.

Here again, the annular slit 36 may consist solely of a central extraction orifice, which further improves the alignment of particles during extraction.

Regardless of the selected embodiment, the dynamic mobility selector described above may be coupled to a detector that can count selected particles. For example, this detector could be an optical detector, particularly of the light diffusion type. In this case, the particles to be analyzed are entrained by the gas flow through a light beam produced by a light source. Each particle then diffuses a given quantity of light which is subsequently analyzed by a light-detector. Furthermore, analysis means are also provided to collect and process data.

A dynamic mobility spectrometer may be made by coupling a selector like that described above, with means of varying the air flow $Q_o$ and means of detecting or counting selected particles.

Regardless of the selected embodiment, it is possible to provide means to keep the selector or the selection zone (zone 31 in FIGS. 3A and 3B) at a low pressure. This can increase the average free path of fluid molecules, and therefore increase the Knudsen number Kn and the correction term C(d) (see formulas (3) and (3') above). The result is an increase in $\rho$, B and $V_s$ for a given particle size d (equations (4) and (5)).

Figure 5:
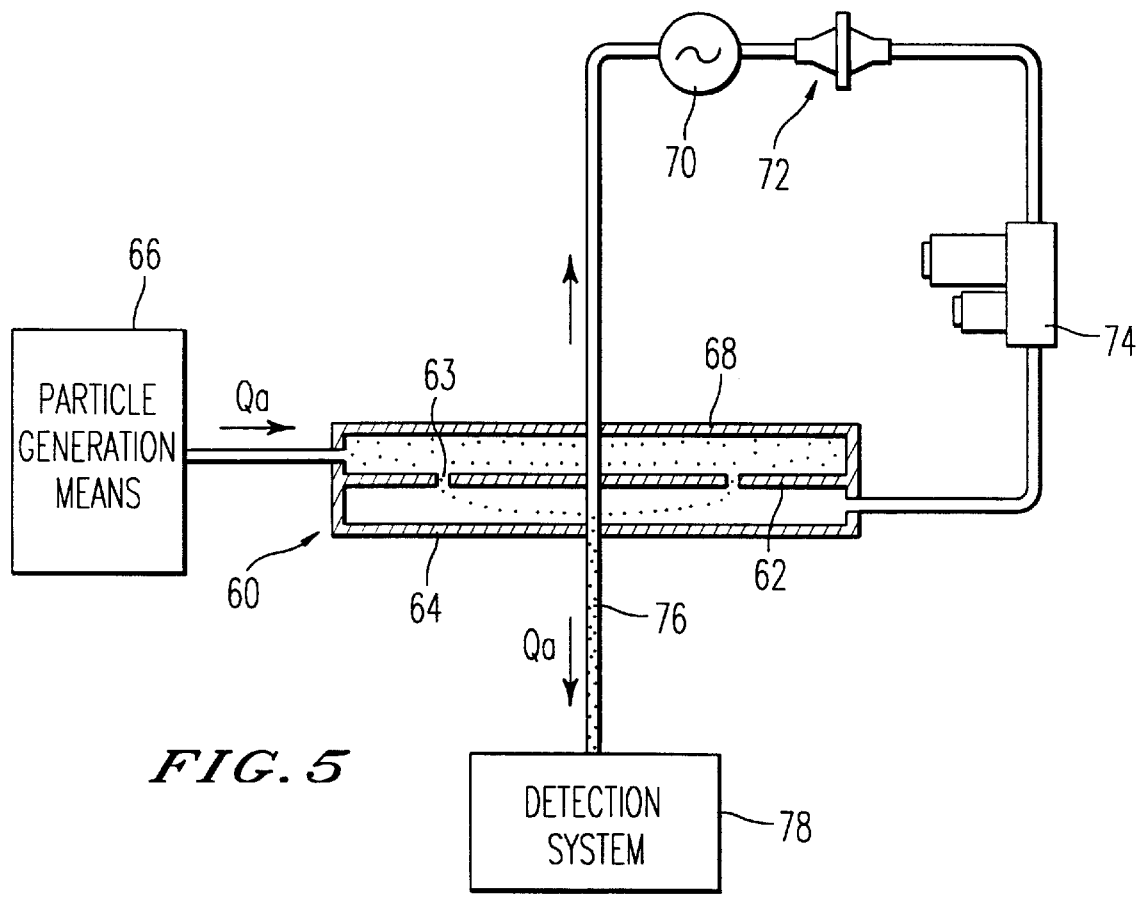
FIG. 5 shows a device according to the invention for measuring the aerodynamic diameter of the particles of an aerosol.

We will now describe a device for measuring the aerodynamic diameter of aerosol particles, with reference to FIG. 5. Reference 60 in FIG. 5 shows a selection device as described above in relation to FIG. 3B, and references 62 and 64 refer to parallel and concentric disks respectively defining the dynamic selection zone. Particle generation means 66 put particles to be characterized into suspension. For example, these means may include a powder or liquid spraying system using a pneumatic method. A gas sample containing the particles is then continuously introduced with a flow $Q_a$ through an annular slit 63 located in the upper disk 62 of the selector 60. For example, the particles may be introduced through an intermediate stage defined by disk 62 and another disk 68 located above disk 62. The laminar, centripetal and stable flow is established in selector 60 by a circuit containing a pump 70, a filter 72 and a flow regulator 74. Particles selected through the selector outlet orifice pass through a duct 76 towards a detection system 78. As explained above, particles counted by detector 78 are particles which have a relaxation time (and therefore a sedimentation speed and an aerodynamic diameter) determined by flow $Q_0$.

As we have already seen, a selector according to the invention may be used as a mono-dispersed aerosol generator; all particles extracted from the selector have the same aerodynamic diameter. All that is necessary to modify the diameter is to modify the flow $Q_0$.

Another example of an application concerns a device for measuring the particle size of aerosols as a function of their aerodynamic diameters. The particle size of the aerosol introduced into the selector may be determined by measuring the concentration of particles that are outlet from the selector through the central hole or through the extraction slit for different flows $Q_0$. This is done by using the transfer function and the different selector parameters. For a flow $Q_0$, the response $R(Q_0)$ of a detector placed at the outlet from the central hole or the annular extraction slit is given by the following relation:

$$R(Q_0) = \int_o^{\infty} Q_a N(d_p) P(d_p, Q_o) d\, d_p$$

where $Q_a$ represents the aerosol injection flow, $P(d_p, Q_0)$ is the selector transfer function which is actually the probability of extracting particles of diameter $d_p$ for a flow $Q_o$, and $N(d_p)dd_p$ is the unknown distribution function. If the operation is repeated for several values of flow $Q_0$, different responses $R(Q_0)$ are obtained, and thus a system of equations that can be used to determine the distribution function $N(d_p)dd_p$ by conventional mathematical inversion techniques.

The invention is particularly suitable for particles with sufficient inertia to be able to form a sediment in the selector, and particularly super-micronic particles, i.e. particles with a diameter exceeding 1 μm and particularly particles between about 2 and 20 μm.

We claim:

1. A dynamic mobility selector for aerosol particles contained in an atmosphere, containing:
    a first and second coaxial disk, separated and parallel, the space between the two disks defining a dynamic selection zone communicating with the aerosol to be examined through an annular slit of radius $r_1$ formed in the first disk, and
    a central intake through which a laminar, centripetal, and stable air flow is circulated in the dynamic selection zone.

2. A dynamic mobility selector according to claim 1, further comprising: an annular opening having an average radius $r_2$ ($r_2 < r_1$) formed in the second disk.

3. A dynamic mobility selector according to claim 2, further comprising:
    a third disk facing the second disk,
    means for injecting a radial and laminar air flow into the space between the second and third disks, said air flow starting from the periphery of the second and third disks, and
    a central extraction orifice formed in the third disk.

4. A dynamic mobility selector according to claims 2 or 3, wherein the opening provided in the second disk consists solely of a central extraction orifice.

5. A dynamic mobility selector according to claims 2 or 3, further comprising: an aerosol collector mounted at an outlet of the selector.

6. A dynamic mobility selector according to claims 1 or 2, further comprising: means for keeping the space between the first and second disks at low pressure.

7. A dynamic mobility selector according to claims 1 or 2, further comprising: means for varying the air flow introduced between the first and second disks.

8. A dynamic mobility spectrometer for particles of an aerosol contained in an atmosphere, comprising:

a dynamic mobility selector including
   a first and second coaxial disk separated and parallel the space between the two disks defining a dynamic selection zone communicating with the aerosol to be examined through an annular slit of radius $r_1$ formed in the first disk,
   a central intake through which a laminar, centripetal, and stable air flow is circulated in the dynamic selection zone, and
   an annular opening having an average radius $r_2$ ($r_2<r_1$) formed in the second disk;

means for varying the air flow between the first and second disks; and means for detecting the selected particles.

9. A dynamic mobility spectrometer according to claim 8, wherein the detection means is an optical detection means.

10. A device for measuring the particle size of an aerosol, comprising:

a dynamic mobility selector including
   a first and second coaxial disk, separated and parallel, the space between the two disks defining a dynamic selection zone communicating with the aerosol to be examined through an annular slit of radius $r_1$ formed in the first disk,
   a central intake through which a laminar, centripetal, and stable air flow is circulated in the dynamic selection zone, and
   an annular opening having an average radius $r_2$ ($r_2<r_1$) formed in the second disk;

means for varying the air flow between the first and second disks;

means for detecting selected particles; and means for calculating the particle size of the aerosol.

* * * * *